United States Patent
Fang et al.

(10) Patent No.: US 9,980,916 B2
(45) Date of Patent: May 29, 2018

(54) NON-GELATIN ENTERIC SOFT CAPSULES

(71) Applicant: PATHEON SOFTGELS INC, High Point, NC (US)

(72) Inventors: Qi Fang, Oak Ridge, NC (US); Josh Heflin, Asheboro, NC (US); Madhu Hariharan, Greensboro, NC (US)

(73) Assignee: Patheon Softgels, Inc., Highpoint, NC (US)

( * ) Notice: Subject to any disclaimer, the term of this patent is extended or adjusted under 35 U.S.C. 154(b) by 0 days. days.

(21) Appl. No.: 14/776,309

(22) PCT Filed: Mar. 14, 2014

(86) PCT No.: PCT/US2014/026947
§ 371 (c)(1),
(2) Date: Sep. 14, 2015

(87) PCT Pub. No.: WO2014/152098
PCT Pub. Date: Sep. 25, 2014

(65) Prior Publication Data
US 2016/0038425 A1    Feb. 11, 2016

Related U.S. Application Data

(60) Provisional application No. 61/792,521, filed on Mar. 15, 2015.

(51) Int. Cl.
*A61K 9/48* (2006.01)
*A61J 3/07* (2006.01)

(52) U.S. Cl.
CPC ............... *A61K 9/4816* (2013.01); *A61J 3/07* (2013.01)

(58) Field of Classification Search
CPC ................................. A61J 3/07; A61K 9/4816
See application file for complete search history.

(56) References Cited

U.S. PATENT DOCUMENTS

| | | | |
|---|---|---|---|
| 5,146,730 A | 9/1992 | Sadek et al. | |
| 5,342,626 A | 8/1994 | Winston, Jr. | |
| 5,356,625 A | 10/1994 | Ying | |
| 5,459,983 A | 10/1995 | Sadek et al. | |
| 6,214,376 B1 | 4/2001 | Gennadios | |
| 6,340,473 B1 | 1/2002 | Tanner et al. | |
| 6,482,516 B1 | 11/2002 | Sadek et al. | |
| 6,949,256 B2 * | 9/2005 | Fonkwe | A61K 9/4816 106/162.1 |
| 7,169,450 B2 * | 1/2007 | Bunick | A61K 9/2072 424/464 |
| 7,887,838 B2 | 2/2011 | Archibald et al. | |
| 8,361,506 B2 | 1/2013 | Ziegler et al. | |
| 2003/0138482 A1 | 7/2003 | Gennadios | |
| 2006/0115527 A1 | 6/2006 | Hassan et al. | |
| 2006/0165778 A1 | 7/2006 | Hassan et al. | |
| 2007/0098786 A1 * | 5/2007 | Chidambaram | A61K 9/4816 424/456 |
| 2012/0269889 A1 | 10/2012 | Shelley et al. | |

FOREIGN PATENT DOCUMENTS

| | | |
|---|---|---|
| EP | 1598062 A1 | 11/2005 |
| EP | 1628643 B1 | 2/2013 |
| WO | 2005004840 A2 | 1/2005 |
| WO | 2005004840 A3 | 6/2005 |
| WO | 2007044488 A1 | 4/2007 |

OTHER PUBLICATIONS

European Search Report for Appln. No. 14768066.4, dated Jul. 11, 2016.

* cited by examiner

*Primary Examiner* — Michael B. Pallay
(74) *Attorney, Agent, or Firm* — Brinks Gilson & Lione

(57) ABSTRACT

Enteric soft capsules containing carrageenans as the film-forming polymer have been developed. The enteric soft capsules comprise iota carrageenan and kappa carrageenan, methacrylic acid copolymers, modifeid starch fillers, plasticizers, water, and other excipients. Such enteric soft capsules are stable at pH 1.2 for at least 2 hours and dissolve at pH 6.8 within about 30 minutes. Methods for manufacturing enteric soft capsules comprising carrageenans are also exemplified.

1 Claim, No Drawings

NON-GELATIN ENTERIC SOFT CAPSULES

CROSS REFERENCE TO RELATED APPLICATIONS

This application is a national phase application under 35 U.S.C. § 371 from International Patent Application No. PCT/US2014/026947, filed on Mar. 14, 2014, which claims priority to U.S. Provisional Patent Application No. 61/792,521, filed Mar. 15, 2013, each of which is incorporated by reference herein in their entirety.

TECHNICAL FIELD

Described herein are pharmaceutical enteric soft capsules that do not contain gelatin as a film-forming polymer. In particular, compositions and methods for manufacturing enteric soft capsules comprising carrageenans as film forming polymers are described.

BACKGROUND

Carrageenan is a natural hydrocolloid, more particularly a polysaccharide hydrocolloid, which is derived from edible red seaweed, particularly of the species Rhodophyceae. Carrageenan is a carbohydrate polymer of repeating galactose and 3,6-anhydrogalactose (sugar) units that is linear and without significant numbers of branches or substitutions. Most, if not all, of the galactose units on a carrageenan molecule possess a sulfated ester group. The exact position of the sulfate groups, the cations on the sulfate groups, and the possible presence of an anhydrous bridge on the molecule differentiate the various types of carrageenan. The molecules are large and highly flexible and can form helical structures. This gives them the ability to form gels at ambient temperatures.

A need has arisen in recent years for gelatin-alternatives for soft capsule manufacturing. This need was driven primarily by the identification of Bovine Spongiform Encephalitis (BSE) in cattle, a primary source of gelatin used in soft capsules. In addition, vegetarians and consumers with religious restrictions on consuming materials of animal origin have further heightened the need to develop animal-free soft capsules. Animal-free soft capsules have been developed as described in International Patent Application Publication No. WO 2005/004840 and U.S. Pat. Nos. 6,214,376; 6,949,256; and 7,887,838, each of which is fully incorporated by reference herein for such teachings. While such soft gel technologies are useful for gastric delivery, there remains a need for an enteric non-gelatin soft capsule technology.

Accordingly, it is desirable to develop an enteric soft capsule that comprises carrageenans as film-forming agents in place of gelatin. This permits the manufacture of animal-free enteric soft capsules.

SUMMARY

One embodiment described herein is an oral enteric soft capsule shell formed from a gel mass composition comprising: (a) a carrageenan composition; (b) a filler; (c) a methacrylic acid copolymer; (d) one or more plasticizers; (e) an alkaline aqueous solvent; and (f) water. In one aspect described herein, the carrageenan composition comprises about 1% to about 15% of the gel mass. In another aspect described herein, the carrageenan composition comprises about 3% to about 5% of the gel mass. In another aspect described herein, the carrageenan composition comprises iota carrageenan and kappa carrageenan. In another aspect described herein, the weight percentage ratio range of iota carrageenan to kappa carrageenan in the gel mass is about 2.5:1 to about 5:1. In another aspect described herein, the weight percentage ratio range of iota carrageenan to kappa carrageenan in the gel mass is about 3:1 to about 4:1. In another aspect described herein, the iota carrageenan comprises from about 0.5% to about 12% by weight of the gel mass. In another aspect described herein, the iota carrageenan is present in an amount of from about 9% to about 12% by weight of the gel mass. In another aspect described herein, the iota carrageenan comprises from about 2.5% to about 4% by weight of the gel mass. In another aspect described herein, the kappa carrageenan comprises from about 0.5% to about 4% by weight of the gel mass. In another aspect described herein, the kappa carrageenan comprises from about 0.5% to about 1% by weight of the gel mass. In another aspect described herein, the methacrylic acid copolymer comprises about 8% to about 20% of the gel mass. In another aspect described herein, the methacrylic acid copolymer comprises about 9% to about 11% of the gel mass. In another aspect described herein, the weight ratio range of the carrageenan composition to methacrylic acid copolymer is about 3:9 (≈0.3) to about 4:3 (≈1.3). In another aspect described herein, the weight percentage of the carrageenan composition and methacrylic acid copolymer comprises about 12.5% to about 15% of the gel mass. In another aspect described herein, the filler comprises a modified starch. In another aspect described herein, the filler comprises hydroxypropyl starch phosphate. In another aspect described herein, the weight percentage range of filler is about 9% to about 14%. In another aspect described herein, the one or more plasticizers comprise sorbitol, non-crystallizing sorbitol, Sorbitol Special®, corn syrup, maltitol, glycerol, polyethylene glycol, citric acid, citric acid esters, triethyl citrate, or combinations thereof. In another aspect described herein, the one or more plasticizers comprise glycerol, sorbitol, corn syrup, or triethyl citrate. In another aspect described herein, the total weight percentage of plasticizer comprises about 9% to about 12% of the gel mass. In another aspect described herein, the alkali neutralizing agent comprises ammonia. In another aspect described herein, the weight percentage of alkali neutralizing agent comprises from about 1% to about 2% of the gel mass.

In one aspect described herein, the composition further comprises any of the following optional components: a sealant, an opacifier, a coloring, a flavoring, or a pharmaceutically acceptable excipient. In one aspect described herein, the composition further comprises a sealant.

Another embodiment described herein is an enteric soft capsule shell composition comprising: (a) about 3% to about 5% carrageenan composition; (b) about 9% to about 14% of hydroxypropyl starch phosphate; (c) about 9% to about 11% of a methacrylic acid copolymer; (d) about 9% to about 12% of one or more plasticizers comprising glycerol, sorbitol, corn syrup, r triethyl citrate; (e) about 1% to about 2% of ammonia; and (f) water. In one aspect described herein, the weight percentage ratio range of iota carrageenan to kappa carrageenan in the gel mass is about 3:1 to about 4:1. In one aspect described herein, the iota carrageenan comprises from about 2.5% to about 4% by weight of the gel mass and the kappa carrageenan comprises from about 0.5% to about 1% by weight of the gel mass. In one aspect described herein, the weight ratio range of the carrageenan composition to methacrylic acid copolymer is about 3:9 (≈0.3) to about 4:3 (≈1.3). In one aspect described herein, the total weight percentage of the carrageenan composition and methacrylic acid copolymer comprises about 12.5% to about 15% of the gel mass.

Another embodiment described herein is a composition comprising (a) about 2.5% iota carrageenan; (b) about 0.6% iota carrageenan; (c) about 9.2% hydroxypropyl starch phosphate; (d) about 9.7% methacrylic acid copolymer; (e) about 6.3% glycerol; (f) about 2.9 sorbitol or corn syrup; (g) about 1.2% triethyl citrate; (h) about 1.2% ammonia; and (i) about 63% water.

Another embodiment described herein is an enteric soft capsule comprising any of the foregoing compositions or described herein.

Another embodiment described herein is an enteric soft capsule comprising any of the foregoing compositions or described herein further comprising an active ingredient in the matrix fill. In one aspect described herein, the capsule comprises a fill that is liquid, semi-solid, or solid. In another aspect described herein, the capsule shell does not dissolve in simulated gastric fluid (pH 1.2) for at least 2 hours, and begins dissolution in simulated intestinal fluid (pH 6.8) within about 10 minutes. In another aspect described herein, the capsule shell is clear or transparent. In another aspect described herein, the capsule shell is transparent and colored. In another aspect described herein, the thickness of the capsule shell is from about 0.010 inches to about 0.050 inches.

Another embodiment described herein is a method for preparing an enteric soft capsule gel mass composition comprising: (a) combining dry shell components comprising carrageenan, filler, and methacrylic acid copolymer, together to form a dry mixture; (b) adding plasticizer, solvent, and alkali neutralizing agent to the dry mixture with agitation to form a wet mixture; (c) heating the wet mixture with agitation and applying vacuum to form a gel mass; (d) heating the gel mass for an additional period; (i) transferring the heated gel mass to an extruder; (ii) extruding the gel mass to form ribbons or films; and (iii) forming an enteric soft capsule using rotary die technology; or (i) cooling the gel mass and grinding the gel mass into pellets; (ii) extruding the cooled gell mass pellets to form ribbons or films; and (iii) forming an enteric soft capsule using rotary die technology; and (e) drying the enteric soft capsules. In one aspect described herein, the wet mixture is heated to about 30° C. to about 90° C. while vacuum is applied for between about 1 hours to about 6 hours to form a gel mass. In another aspect described herein, the gel mass is heated to about 75° C. to about 90° C. for between about 0.5 hours to about 72 hours.

Another embodiment described herein is an enteric soft capsule formed according to the foregoing method or any appropriate methods described herein comprising the enteric soft capsule composition of any of the foregoing compositions or compositions described herein. In another embodiment described herein, the foregoing enteric soft capsule further comprises an active ingredient in the matrix fill. In another aspect described herein, the enteric soft capsule shell is stable at pH 1.2 for at least 2 hr. In another aspect described herein, the enteric soft capsule shell dissolves at pH 6.8 within 30 min. In another aspect described herein, the capsule comprises a fill that is liquid, semi-solid, or solid. In another aspect described herein, the capsule shell is clear or transparent. In another aspect described herein, the capsule shell is transparent and colored. In another aspect described herein, the thickness of the capsule shell is from about 0.010 inches to about 0.050 inches.

Another embodiment described herein is pharmaceutical composition comprising an enteric soft capsule as described herein.

Another embodiment described herein is method for treating, ameliorating the symptoms of, or delaying the onset of a medical condition by providing a subject in need thereof with a pharmaceutical composition, further comprising an active pharmaceutical agent.

DETAILED DESCRIPTION

Described herein are compositions and methods for manufacturing enteric soft capsules that do not contain gelatin as a film-forming polymer.

One embodiment described herein is an enteric soft capsule composition comprising carrageenans as film forming polymers. The enteric soft capsule shell can comprise one or more film forming polymers, one or more enteric polymers, one or more plasticizers, one or more neutralizing agents, one or more solvents, and optionally sealants, colorings, flavorings, or other conventionally accepted pharmaceutical excipients or additives.

As used herein, the phrase "enteric soft gel capsule composition," "enteric soft capsule gel mass," "gel mass," or "enteric soft capsule shell" are used interchangeably and have the same meaning, i.e., a non-animal enteric soft capsule composition that does not comprise gelatin as a film-forming polymer. Typically as used herein, "enteric soft gel capsule composition" or "gel mass" refer to enteric soft gel capsule compositions prior to forming the enteric soft capsule and "enteric soft capsule shell" refers to the enteric capsule shell after having been formed into an enteric soft capsule, for example, by using rotary die encapsulation.

The enteric soft capsules described herein can be used for oral delivery of active pharmaceutical agents that are irritating to the stomach, that are sensitive to the acidity of the stomach, or that have unpleasant tastes or odors. The enteric soft capsules described herein do not dissolve in the gastric environment (pH ca. 1.2), but readily dissolve in the intestinal environment (pH ca. 6.8).

Enteric soft capsules are described generally in International Patent Application Publication No. WO 2004/030658 and U.S. Patent Application Publication No. US 2006/0165778, both of which are incorporated by reference herein for such teachings.

Examples of film-former polymers that are useful for creating non-animal/non-gelatin enteric soft capsules described herein are kappa carrageenan, iota carrageenan, lambda carrageenan, or combinations thereof.

Examples of enteric, acid-insoluble polymers, as described herein, are acrylic and methacrylate acid copolymers, cellulose acetate phthalate (CAP), cellulose acetate butyrate, hydroxypropylmethylcellulose phthalate (HP-MCP), algenic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT® (Evonik Industries AG, Essen, Germany), are provided as powder or aqueous dispersions. In some aspects, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D;

EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one embodiment, the enteric polymer is poly(meth)acrylate is EUDRAGIT® L 100, a methacrylic acid copolymer, Type A. Acid-insoluble polymer specifications are detailed in the United States Pharmacopoeia and in various monographs.

Useful plasticizers as described herein are glycerol, sorbitol, Sorbitol Special® (SPI Pharma), non-crystallizing sorbitol, Polysorb® sorbitol 85/70/00 (Roquette), corn syrup, polyethylene glycol, 1,2-propylene glycol, acetyltriethyl citrate, dibutyl phthalate, dibutyl sebacate, triacetine, polydextrose, maltodextrin, citric acid, citric acid esters, such as triethyl citrate, or combinations thereof. The weight ratios between the film-forming polymer, the acid-insoluble enteric polymer, filler, and plasticizer are adjusted so that the gel mass is flowable and not too viscous, and can be made into enteric soft capsules. In one particular embodiment described herein, the plasticizer comprises at least one of glycerol, sorbitol, corn syrup, malatol, triethyl citrate, or mixtures or combinations thereof.

Useful fillers or bulking agents, as described herein, are hydroxypropyl starch phosphate, acacia, alginic acid, microcrystalline cellulose, carboxymethylcellulose, hydroxypropyl methylcellulose, methylcellulose, ethylcellulose, pregelatinized starch, potato starch, tapioca starch, rice starch, corn starch, wheat starch, pea starch, modified starches, pregelatinized starch, microcrystalline cellulose, hydroxypropyl methylcellulose, lactose, dextrates, dextrin, dextrose, maltodextrin, glucose, sucrose, powdered sugar, sucrose syrup, mannitol, gums like xanthan gum, tragacantha, guar gum, acacia gum, arabic gum, ferula gummosa boiss, gum olibanum, beilschmiedia seed gum, aegle marmelos gum, okra gum, cassia roxburghii seeds gum, kaolin, talc, bentonite, calcium phosphates, calcium carbonate, magnesium carbonate, magnesium oxide, calcium sulphate, hydrogenated sodium chloride, potassium chloride, combinations or mixtures thereof, and others known in the art. Other useful fillers are N-Lok®, (starch sodium octenyl succinate), Hi-Cap™, and Ultra Sperse® M.

In some embodiments, the enteric soft capsule shell composition comprises a sealant polymer that imparts moisture protection to the capsule shell. In one aspect, the sealant can be a methacrylic acid copolymer, hydroxypropylmethylcellulose, or a proprietary sealant such as Kollicoat® Protect (BASF). In one aspect described herein, the sealant is Kollicoat® Protect.

In one embodiment described herein, enteric soft capsule shell compositions can be made by dissolving the enteric acid-insoluble polymer in an aqueous solution of an alkali neutralizing agent such as ammonia, sodium hydroxide, potassium hydroxide, or liquid amines such as triethanol amine or ethylene diamine. The amount of alkali is adjusted to give a final pH value of the gel mass less than or equal to about pH 9.0. In one embodiment, the final pH does not exceed 8.5. In one embodiment the volatile alkali neutralizing agent, ammonia, is preferred. The film-forming polymer(s) and filler can be combined with the plasticizer and solvent and then blended with the acid-insoluble gel to make a final homogeneous mix in a heat-controlled vessel and can be degassed by using vacuum. The fugitive ammonia evaporates during degassing. Using the foregoing process, the alkali concentrations do not require an additional step such as neutralizing with acid in order to neutralize the gel mass.

In another embodiment described herein, the enteric soft capsule shell can be made by using an aqueous dispersion of the acid-insoluble polymer by adding alkaline materials such as ammonium, sodium, or potassium hydroxides, other alkalis, or a combination thereof that will cause the enteric acid-insoluble polymer to dissolve. The plasticizer-wetted, film-forming polymer(s) and filler can then be mixed with the solution of the acid-insoluble polymer. In one embodiment, enteric acid-insoluble polymers in the form of salts of the above-mentioned bases or alkalis can be dissolved directly in water and mixed with the plasticizer-wetted, film-forming polymer.

In one embodiment described herein, the enteric soft capsule has the composition of Table 1, including all possible iterations of the specified ranges that provide 100% for the total weight percentage, including or excluding the optional sealants, colorings, flavorings, or excipients.

TABLE 1

Enteric Soft Capsule Shell Composition

| Component | Exemplary Component | Composition Range (%) |
|---|---|---|
| Film-forming polymer | Carrageenans (Iota + Kappa) | 0.5-15 (I: 0.5-12/ K: 0.5-4) |
| Filler (bulking agent) | Hydroxypropyl starch phosphate | 10-20 |
| Enteric, acid insoluble polymer | Methacrylic Acid Copolymer | 8-20 |
| Plasticizer | Glycerol, Sorbitol, Triethyl citrate | 4-20 |
| Alkali neutralizing agent | NH$_4$OH (30%), NaOH | 1-5 |
| Solvent | Water | 50-70 |
| Sealant (optional) | Kollicoat ® Protect | 1-5 |
| Opacifier (optional) | Titanium dioxide | 0.5-5 |
| Coloring (optional) | Various | 0.005-1 |
| Flavoring (optional) | Various | 0.005-2 |
| Excipients (optional) | Various | 1-5 |

In another embodiment described herein, the weight percentage of the total carrageenan (e.g., a carrageenan composition) in the enteric soft gel composition is about 1% to about 15%. In another embodiment, the weight percentage of the total carrageenan composition in the gel mass is about 3% to about 10%. In another embodiment, the weight percentage of the total carrageenan composition in the gel mass is about 3% to about 5%. In some embodiments, the weight percentage of the total carrageenan composition in the gel mass is about 3% to about 4%. In another embodiment, the weight percentage of the total carrageenan composition in the gel mass is about 3%.

In another embodiment described herein, the weight percentage ratio range of iota carrageenan to kappa carrageenan in the enteric soft gel composition is about 2.5:1 to about 5:1, including all integers within the specified range. In another embodiment, the weight percentage ratio range of iota carrageenan to kappa carrageenan in the gel mass is about 2.5:1 to about 4:1, including all integers within the specified range. In one aspect, the ratio of iota carrageenan to kappa carrageenan in the gel mass is about 4:1. In another aspect, the ratio of iota carrageenan to kappa carrageenan in the gel mass is about 3:1. In another aspect, the ratio of iota carrageenan to kappa carrageenan in the gel mass is about 3.5:1. In another aspect, the ratio of iota carrageenan to kappa carrageenan in the gel mass is about 3.8:1.

In another embodiment described herein, the weight percentage of iota carrageenan in in the enteric soft gel composition is about 0.5% to about 12%, including all integers within the specified range. In another embodiment, the weight percentage of iota carrageenan in the gel mass is about 2% to about 10%, including all integers within the specified range. In another embodiment, the weight percentage of iota carrageenan in the gel mass is about 2.5% to about 4%, including all integers within the specified range. In one aspect, the weight percentage of iota carrageenan in the gel mass is about 4%. In another aspect, the weight percentage of iota carrageenan in the gel mass is about 3%. In another aspect, the weight percentage of iota carrageenan in the gel mass is about 2.5%.

In one embodiment described herein, the weight percentage of kappa carrageenan in the enteric soft gel capsule composition is about 0.5% to about 4%, including all integers within the specified range. In another embodiment, the weight percentage of kappa carrageenan in the gel mass is about 0.5% to about 2.5%, including all integers within the specified range. In another embodiment, the weight percentage of kappa carrageenan in the gel mass is about 0.5% to about 1%, including all integers within the specified range. In one aspect, the weight percentage of kappa carrageenan in the gel mass is about 1%. In another aspect, the weight percentage of kappa carrageenan in the gel mass is about 0.8%. In another aspect, the weight percentage of kappa carrageenan in the gel mass is about 0.5%.

In another embodiment described herein, the weight percentage of enteric acid insoluble polymer in the enteric soft gel composition is about 8% to about 20%. In another embodiment, the weight percentage of enteric acid insoluble polymer in the gel mass is about 9% to about 11%. In another embodiment, the weight percentage of enteric acid insoluble polymer in the gel mass is about 9% to about 10%. In some embodiments, the weight percentage of enteric acid insoluble polymer in the gel mass is about 9.8%. In another embodiment, the weight percentage of enteric acid insoluble polymer in the gel mass is about 9.7%.

In one embodiment described herein, the weight percentage range of total polymer content (i.e., film forming polymer (e.g., total carrageenan content) and enteric acid-insoluble polymer) of the enteric soft capsule composition described herein is about 9% to about 35%, including all integers within the specified range. In another embodiment, the range of total polymer weight percentage in the gel mass is about 12% to about 20%. In another embodiment, the range of total polymer weight percentage in the gel mass is about 12.5% to about 15%. In one aspect, the total polymer weight percentage in the gel mass is about 16%. In another aspect, the total polymer weight percentage in the gel mass is about 15%. In another aspect, the total polymer weight percentage is about 14%. In another aspect, the total polymer weight percentage in the gel mass is about 13%. In one aspect, the total polymer weight percentage in the gel mass is about 12.8%.

In one embodiment described herein, the weight percentage range of total plasticizer in the enteric soft capsule composition is about 4% to about 20%, including all iterations of integers with the specified range. In another embodiment, the weight percentage range of total plasticizer in the gel mass is about 9% to about 12%, including all iterations of integers with the specified range. In one aspect, the total plasticizer weight percentage in the gel mass is about 11%. In another aspect, the total plasticizer weight percentage is about 10%. In another aspect, the total plasticizer weight percentage in the gel mass is about 10.5%. In another aspect, the total plasticizer weight percentage in the gel mass is about 9%. In one aspect, the total plasticizer weight percentage in the gel mass is about 10.4%. In another aspect, the total plasticizer weight percentage in the gel mass is about 10.5%.

In one embodiment described herein, the weight percentage range of filler or bulking agent in the enteric soft capsule composition is about 8% to about 20%, including all iterations of integers with the specified range. In another embodiment, the weight percentage range of filler in the gel mass is about 9% to about 14%, including all iterations of integers with the specified range. In another embodiment, the weight percentage range of filler in the gel mass is about 9% to about 12%, including all iterations of integers with the specified range. In one aspect, the filler weight percentage in the gel mass is about 13%. In another aspect, the filler weight percentage in the gel mass is about 12%. In another aspect, the total plasticizer weight percentage is about 11%. In another aspect, the filler weight percentage in the gel mass is about 10%. In one aspect, the filler weight percentage is about 9%. In another aspect, the total plasticizer weight percentage in the gel mass is about 9.2%.

In one embodiment described herein, the alkali neutralizing agent is ammonia (e.g., ammonium hydroxide; 30% w/v) that is added to comprise a weight percentage of about 1 to about 5% of the total enteric soft capsule composition. The ammonia is added neat and dilution is not considered in calculating the weight percentage; thus, the weight percentage indicated is the weight percentage of 30% ammonium hydroxide added to the composition. In one aspect, ammonia comprises a weight percentage of about 2% of the gel mass. In another aspect, ammonia comprises a weight percentage of about 1.7% of the gel mass. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In some aspects, practically all of the fugitive ammonia is evaporated from the gel mass except for ammonium ions comprising salts with other components of the composition.

In one embodiment described herein, the weight ratio range of film forming polymer (i.e., total carrageenan composition) to enteric acid insoluble polymer (film forming: enteric) in the enteric soft gel composition is about 3:9 (≈0.3) to about 4:3 (≈1.3) (i.e., ≈0.3-1.3), including all ratios within the specified range. In some aspects, the ratio of film forming polymer to enteric acid insoluble polymer in the gel mass is about 1:3 (≈0.33), about 1:2.5 (≈0.4), about 1:2 (≈0.5), about 1:1.6 (≈0.6), about 1:1.25 (≈0.8), about 1:1 (≈1), about 1.1:1 (≈1.1), about 1.21 (≈1.2), or about 1.3:1 (≈1.3). In one aspect, the ratio of film forming polymer to enteric acid insoluble polymer in the gel mass is about 1:2.5 (≈0.4). In another aspect, the ratio of film forming polymer to enteric acid insoluble polymer is about 1:3 (≈0.3).

In one embodiment described herein, the weight ratio range of film forming polymer (i.e., total carrageenan composition) to filler (e.g., hydroxypropyl starch phosphate) in the enteric soft gel composition is about 3:9 (≈0.3) to about 4:3 (≈1.3) (i.e., ≈0.3-1.3), including all ratios within the specified range. In some aspects, the ratio of film forming polymer to filler in the gel mass is about 1:3 (≈0.33), about 1:2.5 (≈0.4), about 1:2 (≈0.5), about 1:1.6 (≈0.6), about 1:1.25 (≈0.8), about 1:1 (≈1), about 1.1:1 (≈1.1), about 1.21 (≈1.2), or about 1.3:1 (≈1.3). In one aspect, the ratio of film forming polymer to filler in the gel mass is about 1:2.5 (≈0.4). In another aspect, the ratio of film forming polymer to filler in the gel mass is about 1:3 (≈0.3).

In one embodiment described herein, the weight ratio range of enteric polymer to filler (e.g., hydroxypropyl starch phosphate) in the enteric soft gel composition is about 1:1.4 (≈0.7) to about 1.2:1 (≈1.2) (i.e., ≈0.7-1.2), including all ratios within the specified range. In some aspects, the ratio of film forming polymer to filler in the gel mass is about 1:1.4 (≈0.7), about 1:1.25 (≈0.8), about 1:1.1 (≈0.9), about 1:1 (≈1), or about 1.1:1 (≈1.1). In one aspect, the ratio of film forming polymer to filler in the gel mass is about 1.1:1 (≈1.1).

In one embodiment described herein, the weight ratio range of total plasticizer to film forming polymer (total carrageenan) in the enteric soft gel composition is about 1:1.25 to 4:1 (i.e., ≈0.8-4), including all ratios within the specified range. In one aspect, the weight ratio of total plasticizer to film forming polymer in the gel mass is about 3.4:1(≈3.4). In another aspect, the weight ratio of total plasticizer to film forming polymer in the gel mass is about 3.1:1 (≈3.1). In another aspect, the weight ratio of total plasticizer to film forming polymer in the gel mass is about 2.7:1 (≈2.7). In another aspect, the weight ratio of total plasticizer to film forming polymer in the gel mass is about 1.4:1 (≈1.4). In another aspect, the weight ratio of total plasticizer to film forming polymer in the gel mass is about 1:1.25 (≈0.8).

In one embodiment described herein, the weight ratio range of total plasticizer to enteric polymer in the enteric soft gel composition is about 1:1.24 to about 1.1:1 (≈0.8-1.1), including all ratios within the specified range. In one aspect, the weight ratio of total plasticizer to enteric polymer in the gel mass is about 1.1:1 (≈1.1). In another aspect, the weight ratio of total plasticizer to enteric polymer in the gel mass is about 1:1 (≈1). In another aspect, the weight ratio of total plasticizer to enteric polymer in the gel mass is about 1:1.1 (≈0.9).

In one embodiment described herein, the weight ratio range of total plasticizer to total polymer (i.e., film forming and enteric) in the enteric soft gel composition is about 1:2 to about 1:1.1 (i.e., ≈0.50-0.9), including all ratios within the specified range. In one aspect, the weight ratio range of total plasticizer to total polymer in the gel mass is about 1:1.25 (≈0.80). In another aspect, the weight ratio range of total plasticizer to total polymer in the gel mass is about 1:1.4 (≈0.7). In another aspect, the weight ratio range of total plasticizer to total polymer in the gel mass is about 1:1.6 (≈0.6). In another aspect, the weight ratio range of total plasticizer to total polymer in the gel mass is about 1:2 (≈0.5).

In one embodiment described herein, the weight ratio range of total plasticizer to filler or bulking agent (e.g., hydroxypropyl starch phosphate) in the enteric soft gel composition is about 1:1.16 to about 1.2:1 (≈0.6-1.2), including all ratios within the specified range. In one aspect, the weight ratio of total plasticizer to enteric polymer in the gel mass is about 1.1:1 (≈1.1). In another aspect, the weight ratio of total plasticizer to enteric polymer in the gel mass is about 1:1.1 (≈0.9). In another aspect, the weight ratio of total plasticizer to enteric polymer is about 1:1.14 (≈0.7). In another aspect, the weight ratio of total plasticizer to enteric polymer in the gel mass is about 1:1.16 (≈0.6).

In one embodiment described herein, the solvent comprises about 50% to about 70% of the enteric soft capsule composition, including all integers within the specified range. In one embodiment, the solvent is water. The quantity of water in the composition varies depending on the quantities of the other ingredients. For example, the quantity of opacifier, coloring, flavoring, or other excipients can change the percentage of water present the composition. In one embodiment, the weight percentage of water is as much as suffices to bring the total weight percentage to 100% (i.e., quantum sufficiat; q.s.). In another embodiment, the water comprises about 70%, about 60%, about 50%, about 40%, or about 30%, of the enteric soft capsule composition. In another embodiment, water comprises about 50% to about 70% of the enteric soft capsule composition. In another embodiment, water comprises about 60% of the gel mass composition. In one embodiment, water comprises about 63% of the gel mass composition.

In one embodiment described herein, the final moisture (water) content of the enteric soft capsule shell formed from the compositions described herein is from about 8% to about 15%, including all integers within the specified range. In another embodiment, the moisture content of the enteric soft capsule shell is about 8% to about 12%, including all integers within the specified range. In one aspect, the final moisture content of the enteric soft capsule shell is about 8%. In one aspect, the final moisture content of the enteric soft capsule is about 9%. In one aspect, the final moisture content of the enteric soft capsule shell is about 10%. In one aspect, the final moisture content of the enteric soft capsule shell is about 11%. In another aspect, the final moisture content of the enteric soft capsule shell is about 12%.

In one embodiment described herein, the enteric soft capsule described herein comprises a composition of about 3% film forming polymer; about 10% enteric, acid insoluble polymer; about 10% filler; about 10% plasticizer; about 1% alkali neutralizing agent; about 2% sealant; and about 60% solvent.

In one embodiment described herein, the enteric soft capsule has the exemplary composition shown in Table 2.

TABLE 2

Exemplary Enteric Soft Capsule Shell Composition

| Component | Percent weight |
|---|---|
| Iota Carrageenan | 2.5 |
| Kappa Carrageenan | 0.6 |
| Hydroxypropyl starch phosphate | 9.2 |
| Methacrylic Acid Copolymer (EUDRAGIT ® L 100) | 9.7 |
| Glycerol | 6.3 |
| Sorbitol Special ® | 2.9 |
| Triethyl citrate | 1.2 |
| Ammonium hydroxide (30% w/v) | 1.7 |
| Water | 63.4 |
| Kollicoat ® Protect (optional) | 2.4 |
| TOTAL | 100% |
| Components and Relational Ratios | |
| Final pH | 8.5-9.0 |
| Total Carrageenan | 3.1 |
| Total Polymer (Carrageenan + Enteric) | 12.8 |
| Total Plasticizer | 10.5 |
| Starch + Enteric | 18.9 |
| Ratio Iota Carrageenan to Kappa Carrageenan | 4.0 |
| Ratio Carrageenan to Enteric | 0.3 |
| Ratio Carrageenan to Starch | 0.3 |
| Ratio of Enteric to Starch | 1.1 |
| Ratio of Plasticizer to Total Polymer | 0.8 |
| Ratio of Plasticizer to Carrageenan | 3.4 |
| Ratio of Plasticizer to Enteric | 1.1 |
| Ratio of Plasticizer to Starch | 1.1 |
| Moisture content in dried enteric soft capsule shell | 8-15% |

In one embodiment described herein, the enteric soft capsule comprises about 3% carrageenan; about 9% hydroxylpropyl starch phosphate; about 6% glycerol; about 3% sorbitol; about 1% triethyl citrate; about 2% ammonia; about 10% poly(methyl) acrylate copolymer; about 60% water, and optionally about 2% sealant (e.g., Kollicoat® Protect).

In some embodiments, the sorbitol can be substituted with corn syrup or malatol (e.g., Lycasin®; hydrogenated glucose syrup).

In other embodiments described herein, the hydroxypropyl starch phosphate can be substituted with pea, potato, or corn starch. In some embodiments, the starch is a modified starch.

The enteric soft capsule composition can optionally include one or more additives such as sealants, opacifiers, preservatives, flavorings, colorings, or other pharmaceutically acceptable excipients, and the like.

Another embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

Films of the enteric soft capsule shell do not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. Enteric soft capsules made using the compositions described herein remain intact in hydrochloric acid or simulated gastric fluid for at least two hours. The capsules readily release the contents upon shifting the pH of the solution to ca. 6.8, such as that of simulated intestinal fluid.

In another embodiment described herein, the final enteric capsule composition provides films of increased strength without substantially compromising film elasticity. Moreover, films made from the enteric soft capsule compositions as described herein can be sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films or ribbons that form the enteric capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

The enteric soft capsules described herein can contain a matrix fill that is liquid, semi-solid, or solid. Capsules prepared as described herein can contain a hydrophobic solution or suspension, such as vegetable oils or shortening, or waxes, or combinations thereof. The matrix fill can be formulated to prevent interaction with the capsule shell components and release the pharmaceutical composition at a specified rate.

The matrix fill can comprise one or more active ingredients and, optionally, one or more pharmaceutically acceptable excipients.

Suitable active ingredients can include, for example, pharmaceutical agents (e.g., therapeutic agents, prophylactic agents, and diagnostic agents), nutraceuticals, vitamins, minerals, or combinations thereof.

In some embodiments described herein, the composition can provide a dosage of an active ingredient for administration. The dosage form can be administered, for example, to a subject, or a subject in need thereof. In one aspect, the subject may be a mammal, or a mammal in need thereof. In one aspect, the dosage form can be administered, for example, to a human or a human in need thereof. In one aspect, the human subject or a human subject in need thereof is a medical patient. In another aspect, the human subject or a human subject in need thereof is a medical patient with a medical condition or in need of treatment or diagnosis of a medical condition.

One embodiment described herein is a pharmaceutical composition comprising an enteric soft capsule as described herein comprising a pharmaceutical agent or agents.

Another embodiment described herein is a method for treating, ameliorating the symptoms of, or delaying the onset of a medical condition by providing a subject in need thereof with a pharmaceutical composition comprising an enteric soft capsule, as described herein, comprising a pharmaceutical agent or agents as (an) active ingredient(s). As used herein, a medical condition can comprise any actual or suspected disease, disorder, or condition that a subject may seek or need medical care therefor. One embodiment described herein is method of treating, ameliorating the symptoms of, or delaying the onset of a medical condition by administering a pharmaceutical agent having a desired therapeutic or biological activity or suspected of having a desired therapeutic or biological activity in a subject in need thereof. In one aspect, the administration of a pharmaceutical agent can be by an enteric soft capsule, as described herein, comprising an active pharmaceutical agent or ingredient.

Examples of pharmaceutical agents that can be included as an active ingredient include agents classified as, for example, an adrenocortical steroid, adrenocortical suppressant, aldosterone antagonist, amino acid, anabolic steroid, androgen, antagonist, anthelmintic, anti-acne agent, anti-adrenergic, anti-allergic, anti-amebic, anti-androgen, anti-anemic, anti-anginal, anti-arthritic, anti-asthmatic, anti-atherosclerotic, antibacterial, anticholelithic, anticholelithogenic, anticholinergic, anticoagulant, anticoccidal, antidiabetic, antidiarrheal, antidiuretic, antidote, antiestrogen, antifibrinolytic, antifungal, antiglaucoma agent, antihemophilic, antihemorrhagic, antihistamine, antihyperlipidemic, antihyperlipoproteinemic, antihypertensive, antihypotensive, anti-infective, anti-infective, anti-inflammatory, antikeratinizing agent, antimalarial, antimicrobial, antimitotic, antimycotic, antineoplastic, antineutropenic, antiparasitic, antiperistaltic, antipneumocystic, antiproliferative, antiprostatic hypertrophy, antiprotozoal, antipruritic, antipsoriatic, antirheumatic, antischistosomal, antiseborrheic, antisecretory, antispasmodic, antithrombotic, antitussive, anti-ulcerative, anti-urolithic, antiviral, appetite suppressant, benign prostatic hyperplasia therapy agent, bone resorption inhibitor, bronchodilator, carbonic anhydrase inhibitor, cardiac depressant, cardioprotectant, cardiotonic, cardiovascular agent, choleretic, cholinergic, cholinergic agonist, cholinesterase deactivator, coccidiostat, contrasting agent, diagnostic aid, diuretic, ectoparasiticide, enzyme inhibitor, estrogen, fibrinolytic, free oxygen radical scavenger, glucocorticoid, gonad-stimulating principle, hair growth stimulant, hemostatic, hormone, hypocholesterolemic, hypoglycemic, hypolipidemic, hypotensive, imaging agent, immunizing agent, immunomodulator, immunoregulator, immunostimulant, immunosuppressant, impotence therapy adjunct, inhibitor, keratolytic, LHRH agonist, liver disorder treatment, luteolysin, mucolytic, mydriatic, nasal decongestant, neuromuscular blocking agent, non-hormonal sterol derivative, oxytocic, plasminogen activator, platelet activating factor antagonist, platelet aggregation inhibitor, potentiator, progestin, prostaglandin, prostate growth inhibitor, prothyrotropin, radioactive agent, regulator, relaxant, repartitioning agent, scabicide, sclerosing agent, selective adenosine A1 antagonist, steroid, suppressant, symptomatic multiple sclerosis, synergist, thyroid hormone, thyroid inhibitor, thyromimetic, amyotrophic lateral sclerosis agents, Paget's disease agents, unstable angina agents, uricosuric, vasoconstrictor, vasodilator, vulnerary, wound healing agent, and xanthine oxidase inhibitor. Further examples of suitable pharmaceutical agents include those as listed in the Merck Index (13$^{th}$ Edition, Wiley, 2001), The United States Pharmacopeia-National Formulary (USP-NF), and the FDA's Orange book, each of which are each incorporated by reference herein for their teachings of pharmaceutically active agents.

Examples of nutraceuticals include, but are not limited to, amino acids, terpenoids (e.g., carotenoid terpenoids and non-carotenoid terpenoids), herbal supplements, homeopathic supplements, glandular supplements, polyphenolics, flavonoid polyphenolics, phenolic acids, curcumin, resveratrol, lignans, glucosinolates, isothiocyanates, indoles, thiosulfonates, phytosterols, anthraquinones, capsaicin, piperine, chlorophyll, betaine, oxalic acid, acetyl-L-carnitine, allantoin, androstenediol, androstendione, betaine (trimethylglycine), caffeine, calcium pyruvate (pyruvic acid), carnitine, carnosine, carotene, carotenoid, choline, chlorogenic acid, cholic acid, chondroitin sulfate, chondroitin sulfate, cholestan, chrysin, coenzyme Q10, conjugated linoleic acid, corosolic acid, creatine, dehydroepiandrosterone, dichlorophen, diindolymethane, dimethylglycine, dimercapto succinic acid, ebselen, ellagic acid, enzymes, fisetin, formonetin, glucaric acid (glucarate), glucosamine (HCl or sulfate), glucosamine (N-acetyl), glutathione, hesperidine, hydroxy-3-methylbutyric acid, 5-hydroxytryptophan, indole-3-carbinol, inositol, isothiocyanates, linolenic acid-gamma, lipoic acid (alpha), melatonin, methylsulfonylmethane, minerals, naringin, pancreatin, para-aminobenzoic acid, paraben (methyl or propyl), phenolics, phosphatidylcholine, phosphatidylserine, phospholipids, phytosterols, progesterone, pregnenolone, omega-3 fatty acids, quercetin, resveratrol, D-ribose, rutin, S-adenosylmethionine, salicylic acid, sulforaphane, tartaric acid, taxifolin, tetrahydropalmatine, theophyline, theobromine, tigogenin, troxerutin, tryptophan, tocotrienol (alpha, beta, and gamma), zeaxanthin, gingko biloba, ginger, cat's claw, hypericum, aloe vera, evening primrose, garlic, capsicum, dong quai, ginseng, feverview, fenugreek, echinacea, green tea, marshmallow, saw palmetto, tea tree oil, fish oil, payllium, kava-kava, licorice root, manonia aquifolium, hawthorne, hohimbr, tumeric, witch Hazel, valerian, mistletoe, bilberry, bee pollen, peppermint oil, beta-carotene, genistein, lutein, lycopene, the polyphenols, and the like. Further examples of suitable nutraceuticals include those listed in Handbook of Nutraceuticals and Functional Foods, edited by Robert E. C. Wildman, CRC Press (2001), which is incorporated by reference herein the teachings on nutraceuticals.

Other useful pharmaceutical agents that can be included as an active ingredients include fish oils, egg oils, squid oils, krill oils, nut oils, seed oils; soy oils, avocado oils, seabuckthorn seed or berry oils, clary sage seed oils, algal oils, flaxseed oils, sacha ichi oils, echium oils, hemp oils, omega-3 fatty acids, polyunsaturated omega-3 fatty acids, hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA), clupanodonic acid), docosahexaenoic acid (DHA, cervonic acid), tetracosapentaenoic acid, tetracosahexaenoic acid (nisinic acid), and free acids, ethyel esters, or other esters or salts thereof. In some aspects, the pharmaceutical agent is a highly purified omega-3 fatty acid, ester, or salt thereof.

Vitamins can be administered using the enteric soft capsules described herein. Vitamins include organic substances that are typically considered essential for the normal growth and activity of a subject (e.g., a human or non-human animal patient to whom the composition is to be administered). Examples of vitamins include, but are not limited to vitamin A (retinol), B1 (thiamine), B2 (riboflavin), B complex, B6 (pyridoxine), B12 (cobalamin), C (ascorbic acid), D (cholecalciferol), E (tocopherol), F (linoleic acid), G, H (biotin), and K, and choline, folic acid, inositol, niacin, pantothenic acid, and para-aminobenzoic acid.

Vitamins can also include naturally occurring inorganic substances that are typically considered essential for the normal growth and activity of a subject (e.g., a human or non-human animal patient to whom the composition is to be administered). Examples of minerals include, but are not limited to, boron, calcium, chromium, copper, iron, magnesium, manganese, molybdenum, nickel, phosphorus, selenium, silicon, tin, vanadium, and zinc.

The matrix fill of the enteric soft capsules described herein can optionally include one or more pharmaceutically acceptable excipients. Examples of pharmaceutically acceptable excipients include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinyl pyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; saltforming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.). Diluents commonly used in the art can also be encapsulated within the shell, including water or other solvents, solubilizing agents, and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame oil, glycerol, tetrahydrofurfuryl alcohol, polyethylene glycols, and fatty acid esters of sorbitan, and mixtures of these substances.

Exemplary lipid or lipophilic substances include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; partially hydrogenated oils; beeswax; polyethoxylated beeswax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol monocaprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyldodecanol; myristyl alcohol; isopropyl myristate, isopropyl palmitate, stearic acid, stearyl alcohol, and others known in the art.

Additional solvents or solubility enhancing agents useful for the matrix fills include Capmul® MCM, Captex® 355, Cremophor® RH 40, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol, Lutrol® F 68, Maisine™ 35-1, mannitol, Miglyol® 812, Pearlitol® Flash, Peceol®, polyethylene glycol 400, polyethylene glycol 600, polyethylene glycol 3350, Plurol® Oleique CC 497, Povidone K 17, Povidone K 30, propylene glycol, and sodium lauryl sulfate.

In some embodiments, the matrix fill can include a release regulator such as a fatty acid salt, fatty acid ester, or fatty acid polyoxyethylene derivative. The release regulator can also be a surfactant having a hydrophilic/lipophilic balance (HLB) value between about 2 and about 40. The HLB characteristic of surfactants can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993), which is incorporated by reference herein for such teachings.

Additional pharmaceutical excipients include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Alkalizing agents (ammonia solution, ammonium carbonate, diethanolamine, diisopropanolamine, potassium hydroxide, sodium bicarbonate, sodium borate, sodium carbonate, sodium hydroxide, trolamine); Antifoaming agents (dimethicone, simethicone); Antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celluloses, hydroxyalkyl, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (Bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely represents the classes of pharmaceutically acceptable excipients that may be used in oral dosage forms as described herein.

In certain embodiments, the matrix fill is a liquid (e.g., a solution, suspension, or dispersion) or a semisolid (e.g., a paste or gel). In some cases, the active ingredient can be innately a liquid or semisolid. In certain cases, the active ingredient can be prepared as a liquid or semisolid by, for example, by dissolving or otherwise mixing an active ingredient and optionally one or more pharmaceutical adjuvants in a carrier, such as, for example, water, saline, aqueous dextrose, glycerol, glycols (e.g., propylene glycol or polyethylene glycol), ethanol, fatty acids, glycerides, oils, sterols, phospholipids, and the like, to thereby form a solution.

In some embodiments described herein, the enteric soft capsules described herein comprises a matrix fill having controlled or extended release properties. Such controlled or extended release matrix fills are described in International Patent Application Publication No. WO 2005/009409 and U.S. Patent Application Publication No. US 2006/0115527, both of which are incorporated by reference herein for such teachings. In some aspects, the matrix can be configured to provide controlled release, extended release, sustained release, delayed release, or combinations thereof.

Accordingly, one embodiment described herein is a controlled release enteric soft capsule having a shell and a matrix fill, wherein the matrix fill includes an active ingredient.

In some embodiments, the active ingredient can be dispersed or suspended in the liquid carrier. In some embodiments, the active ingredient can be prepared in a self-emulsifying/microemulsifying drug delivery system (SEDDS/SMEDDS). Optionally, the SEDDS system can include an oil, a surfactant, a cosurfactant or solubilizer, and the active ingredient.

The matrix fill can be prepared to contain the active ingredient in the range of 0.005% to 100%, with the balance made up from non-toxic carrier. Methods for preparation of these compositions are known to those skilled in the art. See, for example, Remington's Pharmaceutical Sciences, Mack Publishing Company, Easton, Pa., 15$^{th}$ Edition, 1975, which is incorporated by reference herein for such teachings. The liquid fill can contain 0.001% to 100%, 0.1% to 95%, 1% to 90%, 5% to 70%, or 10% to 50% by weight active ingredient.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the claimed embodiments. All of the various aspects, embodiments, and options disclosed herein can be combined in all variations. The scope of the compositions and methods described herein include all actual or potential combinations of embodiments, aspects, examples, and preferences herein described. All patents and publications cited herein are entirely incorporated by reference herein for the specific teachings thereof.

EXAMPLES

Example 1

Enteric soft capsules as described herein were prepared using the composition shown in

TABLE 3

Table 3 Exemplary Non-Gelatin Enteric Soft Capsule Formulation

| Ingredient | Weight (kg) | % Weight |
| --- | --- | --- |
| Iota Carrageenan | 2.00 | 2.47 |
| Kappa Carrageenan | 0.50 | 0.62 |
| Hydroxypropyl starch phosphate | 7.45 | 9.22 |
| Kollicoat ® Protect (BASF) | 1.96 | 2.43 |
| Glycerol | 5.10 | 6.31 |
| Sorbitol Special ® | 2.35 | 2.91 |
| Water | 51.23 | 63.39 |
| Ammonia (30% w/v) | 1.37 | 1.70 |
| Methacrylic acid copolymer (EUDRAGIT ® L100) | 7.86 | 9.73 |
| Triethyl citrate | 1.00 | 1.24 |
| TOTAL | 80.82 kg | 100% |

Example 2

Manufacturing Process

The shell components were dispensed into a heated vessel under agitation. While mixing, heat and vacuum were applied for 1 to 5 hours. When cooking completes, the gel mass was transferred into another heated vessel and kept at 80° C. for between 0.5-72 hours. The molten gel mass can be directly transferred to extruders via volumetric pumps. Alternatively, the gel mass can also be cooled to between 5-30° C., and then ground into pellets of 0.125 in (3.175 mm) to 0.75 in (19.05 mm). The cooled and ground gel mass pellets were fed to extruders via volumetric feeders.

Ribbons were formed via film extrusion. The formed ribbons were fed to a rotary die encapsulation machine to form soft gel capsules. Compared to gelatin capsules, the wedge and drum temperatures wre much higher (>75° C.). The seam formation takes place via adhesion. The formed capsules were dried in a tumbling dryer for between 15-90 minutes, and then dried on trays in a temperature/humidity controlled tunnel for between 12-96 hours.

Finished capsules can withstand USP paddle disintegration tests in acidic media (pH 1.2) for at least 2 hours and release active agents in buffered media (pH 6.8).

Example 3

Examples of gel mass compositions useful for producing non-animal enteric soft capsules are shown below. Composition components are set forth by weight percentage of the total weight of the gel mass composition.

TABLE 4

Exemplary Enteric Soft Capsule Gel Mass

| Ingredient | Weight Percentage (%) | | | | | |
|---|---|---|---|---|---|---|
| | EX 1 | EX 2 | EX 3 | EX 4 | EX 5 | EX 6 |
| Iota Carrageenan | 3.0 | 4.0 | 2.8 | 3.0 | 3.2 | 4.0 |
| Kappa Carrageenan | 1.0 | 1.0 | 0.5 | 0.8 | 0.6 | 0.8 |
| Hydroxypropyl starch phosphate | 9.5 | 14 | 11.5 | 11.0 | 9.0 | 13.0 |
| Kollicoat Protect (BASF) | 2.4 | 2.4 | 2.4 | 2.4 | 2.4 | 2.4 |
| Glycerol | 6.2 | 5.0 | 6.1 | 6.5 | 6.2 | 6.5 |
| Sorbitol Special ® | 0 | 2.5 | 2.6 | 2.3 | 3.0 | 2.1 |
| Corn Syrup | 2.9 | 0 | 0 | 0 | 0 | 0 |
| Water | 62.1 | 58.7 | 59.8 | 61.1 | 63.2 | 60.1 |
| Ammonia (30% w/v) | 1.7 | 1.7 | 1.7 | 1.7 | 1.7 | 1.7 |
| Eudragit L100 | 10.0 | 9.5 | 11.0 | 10.0 | 9.5 | 8.5 |
| Triethyl Citrate (TEC) | 1.24 | 1.24 | 1.6 | 1.24 | 1.17 | 0.9 |
| TOTAL | 100 | 100 | 100 | 100 | 100 | 100 |
| Components and Relational Ratios | | | | | | |
| Total Carrageenan | 4.0 | 5.0 | 3.3 | 3.8 | 3.8 | 4.8 |
| Total Polymer (Carrag. + Enter.) | 14.0 | 14.5 | 14.3 | 13.8 | 13.3 | 13.3 |
| Total Plasticizer | 10.3 | 8.7 | 10.3 | 10.0 | 10.4 | 9.5 |
| Starch + Enteric | 19.5 | 23.5 | 22.5 | 21.0 | 18.5 | 21.5 |
| Ratio Iota to Kappa | 3.0 | 4.0 | 5.6 | 3.8 | 5.3 | 5.0 |
| Ratio of Carrageenan to Enteric | 0.4 | 0.5 | 0.3 | 0.4 | 0.4 | 0.6 |
| Ratio of Carrageenan to Starch | 0.4 | 0.4 | 0.3 | 0.3 | 0.4 | 0.4 |
| Ratio of Enteric to Starch | 1.1 | 0.7 | 1.0 | 0.9 | 1.1 | 0.7 |
| Ratio of Plast. to Total Polymer | 0.7 | 0.6 | 0.7 | 0.7 | 0.8 | 0.7 |
| Ratio of Plast. to Carrageenan | 2.6 | 1.7 | 3.1 | 2.6 | 2.7 | 2.0 |
| Ratio of Plasticizer to Enteric | 1.0 | 0.9 | 0.9 | 1.0 | 1.1 | 1.1 |
| Ratio of Plasticizer to Starch | 1.1 | 0.6 | 0.9 | 0.9 | 1.2 | 0.7 |

| Ingredient | Weight Percentage (%) | | | | | |
|---|---|---|---|---|---|---|
| | EX 7 | EX 8 | EX 9 | EX 10 | EX 11 | EX 12 |
| Iota Carrageenan | 3.0 | 3.0 | 3.0 | 6.0 | 8.0 | 10.0 |
| Kappa Carrageenan | 1.1 | 0.9 | 1.0 | 1.7 | 2.3 | 2.3 |
| Hydroxypropyl starch phosphate | 12.0 | 11.0 | 10.0 | 12.0 | 12.0 | 12.0 |
| Kollicoat Protect (BASF) | 2.4 | 0 | 2.4 | 2.4 | 2.4 | 2.4 |
| Glycerol | 6.2 | 6.1 | 5.9 | 6.3 | 6.3 | 6.3 |
| Sorbitol Special ® | 0 | 3.2 | 3.6 | 2.9 | 0 | 2.9 |
| Corn Syrup | 2.8 | 0 | 0 | 0 | 2.9 | 0 |
| Water | 57.3 | 62.3 | 59.8 | 56.0 | 53.4 | 51.4 |
| Ammonia (30% w/v) | 1.7 | 1.7 | 1.7 | 1.7 | 1.7 | 1.7 |
| Eudragit L100 | 12.0 | 10.5 | 11.2 | 9.8 | 9.8 | 9.8 |
| Triethyl Citrate (TEC) | 1.5 | 1.3 | 1.4 | 1.21 | 1.21 | 1.21 |
| TOTAL | 100 | 100 | 100 | 100 | 100 | 100 |
| Components and Relational Ratios | | | | | | |
| Total Carrageenan | 4.1 | 3.9 | 4.0 | 7.7 | 10.3 | 12.3 |
| Total Polymer (Carrag. + Enter.) | 16.1 | 14.4 | 15.2 | 17.5 | 20.1 | 22.1 |
| Total Plasticizer | 10.5 | 10.6 | 10.9 | 10.4 | 10.4 | 10.4 |
| Starch + Enteric | 24.0 | 21.5 | 21.2 | 21.8 | 21.8 | 21.8 |

TABLE 4-continued

Exemplary Enteric Soft Capsule Gel Mass

| | | | | | | |
|---|---|---|---|---|---|---|
| Ratio Iota to Kappa | 2.7 | 3.3 | 3.0 | 3.5 | 3.5 | 4.3 |
| Ratio of Carrageenan to Enteric | 0.3 | 0.4 | 0.4 | 0.8 | 1.1 | 1.3 |
| Ratio of Carrageenan to Starch | 0.3 | 0.4 | 0.4 | 0.6 | 0.9 | 1.0 |
| Ratio of Enteric to Starch | 1.0 | 1.0 | 1.1 | 0.8 | 0.8 | 0.8 |
| Ratio of Plast. to Total Polymer | 0.7 | 0.7 | 0.7 | 0.6 | 0.5 | 0.5 |
| Ratio of Plast. to Carrageenan | 2.6 | 2.7 | 2.7 | 1.4 | 1.0 | 0.8 |
| Ratio of Plasticizer to Enteric | 0.9 | 1.0 | 1.0 | 1.1 | 1.1 | 1.1 |
| Ratio of Plasticizer to Starch | 0.9 | 1.0 | 1.1 | 0.9 | 0.9 | 0.9 |

What is claimed is:

1. A composition for an oral enteric soft capsule shell comprising:
    2.5% iota carrageenan by mass;
    0.6% kappa carrageenan by mass;
    9.2% hydroxypropyl starch phosphate by mass;
    2.4% polyvinyl alcohol-poly ethylene glycol graft copolymer by mass;
    6.3% glycerin by mass;
    2.9% dehydrated liquid sorbitol by mass;
    1.7% ammonium hydroxide (30% w/v) by mass;
    9.7% methacrylic acid copolymer by mass;
    1.2% triethyl citrate by mass; and
    63.4% water by mass;
    wherein the capsule shell is stable at pH 1.2 for at least 2 hours and dissolves at pH 6.8 within 30 minutes.

* * * * *